United States Patent [19]

Dressel et al.

[11] Patent Number: 5,354,749
[45] Date of Patent: Oct. 11, 1994

[54] SULFONYLBENZYL-SUBSTITUTED BENZO- AND PYRIDOPYRIDONES

[75] Inventors: Jürgen Dressel; Peter Fey, both of Wuppertal; Rudolf H. Hanko, Düsseldorf; Walter Hübsch, Wuppertal; Thomas Krämer, Wuppertal; Ulrich E. Müller, Wuppertal; Matthias Müller-Gliemann, Solingen-Ohligs; Martin Beuck, Erkrath; Stanislav Kazda, Wuppertal; Stefan Wohlfeil, Hilden; Andreas Knorr, Erkrath; Johannes-Peter Stasch, Wuppertal, all of Fed. Rep. of Germany

[73] Assignee: Bayer Aktiengesellschaft, Leverkusen, Fed. Rep. of Germany

[21] Appl. No.: 58,548

[22] Filed: May 5, 1993

[30] Foreign Application Priority Data

May 12, 1992 [DE] Fed. Rep. of Germany ....... 4215587

[51] Int. Cl.$^5$ ............. A61K 31/47; A61K 31/435; C07D 217/24; C07D 471/04
[52] U.S. Cl. ............................ 514/234.5; 514/235.2; 514/300; 514/309; 544/127; 544/128; 544/362; 546/122; 546/123; 546/141; 546/142
[58] Field of Search ............. 546/141, 142, 122, 123; 544/127, 128; 514/234.5, 235.2, 300, 309

[56] References Cited

U.S. PATENT DOCUMENTS

| | | | |
|---|---|---|---|
| 3,914,236 | 10/1975 | Lerch et al. | 546/143 |
| 4,946,841 | 8/1990 | Baader et al. | 514/247 |
| 5,162,340 | 11/1992 | Chakravarty et al. | 546/141 |
| 5,254,543 | 10/1993 | Hanko et al. | 546/276 |

FOREIGN PATENT DOCUMENTS

| | | |
|---|---|---|
| 0399731 | 11/1990 | European Pat. Off. . |
| 0399732 | 11/1990 | European Pat. Off. . |
| 0403158 | 12/1990 | European Pat. Off. . |
| 0403159 | 12/1990 | European Pat. Off. . |
| 0407102 | 1/1991 | European Pat. Off. . |
| 0412848 | 2/1991 | European Pat. Off. . |
| 0425211 | 5/1991 | European Pat. Off. . |
| 0456442 | 11/1991 | European Pat. Off. . |
| 0475206 | 3/1992 | European Pat. Off. . |
| 0487252 | 5/1992 | European Pat. Off. . |
| 0512676 | 11/1992 | European Pat. Off. . |
| 0534706 | 3/1993 | European Pat. Off. . |
| 61-45820 | 10/1986 | Japan . |
| 3-178966 | 8/1991 | Japan . |
| 9101001 | 1/1991 | PCT Int'l Appl. . |

OTHER PUBLICATIONS

J. C. Sheehan, S. L. Ledis, J. Am. Chem. Soc. 95, 875 (1973).
F. E. Frerman et al., J. Biol. Chem. 258, 7087–7093 (1983).
N. B. Benoiton, D. Kluroda, Int. Pept. Prot. Res. 17, 197 (1981).
Boyle et al., J. Org. Chem. 1966, 31, 3807.
Cara et al., J. Org. Chem. 1958, 23, 1616.
Sakamoto et al., Chem. Pharm. Bull. 1985, 33, 565.
Sakamoto et al., Chem. Pharm. Bull., 34(7), 2760–5 (1985).
Sakamoto et al., Chem. Pharm. Bull., 33(2), 626–33 (1985).
Nishiwaki et al. Heterocycles 32(5), 1013–16 (1991).
Datta et al., Indian J. Chem., Sect. B, 20B(5), 376–9 (1981).
Sakamoto et al. Chem. Pharm. Bull. (1988), 36, 1890–1894.

Primary Examiner—Bernard Dentz
Attorney, Agent, or Firm—Sprung Horn Kramer & Woods

[57] ABSTRACT

Sulfonylbenzyl-substituted benzo- and pyridopyridones are prepared by reacting corresponding benzo- and pyridopyridones with sulphonylbenzyl compounds. The sulphonylbenzyl-substituted benzo- and pyridopyridones can be employed as active compounds in medicaments, in particular for the treatment of arterial hyper tension and atherosclerosis.

7 Claims, No Drawings

SULFONYLBENZYL-SUBSTITUTED BENZO- AND PYRIDOPYRIDONES

The present invention relates to sulfonylbenzyl-substituted benzo- and pyridopyridones, a process for their preparation and their use in medicaments, in particular as antihypertensive and anti-atherosclerotic agents.

It is known that renin, a proteolytic enzyme, splits off the decapeptide angiotensin I in vivo from angiotensinogen, the angiotensin I in turn being broken down to the antihypertensive octapeptide angiotensin II in the lung, the kidneys or other tissues. The various effects of angiotensin II, such as, for example, vasoconstriction, $Na^+$ retention in the kidney, release of aldosterone in the adrenal and increasing the tonicity of the sympathic nervous system, have a synergistic action in the context of an increase in blood pressure.

Angiotensin II moreover has the property of promoting the growth and multiplication of cells, such as, for example, of cardiac muscle cells and smooth muscle cells, these growing and proliferating to an increased extent under various disease states (for example hypertension, atherosclerosis and cardiac insufficiency).

A possible point for intervention in the renin-angiotensin system (RAS), in addition to inhibition of renin activity, is inhibition of the activity of angiotensin converting enzyme (ACE) and blockage of angiotensin II receptors.

The present invention relates to sulfonylbenzyl-substituted benzo- and pyridopyridones of the general formula (I)

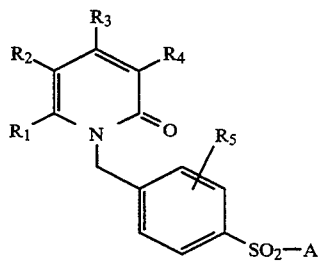

in which $R^1$ and $R^2$ are identical or different and represent hydrogen or cyano, or
  represent straight-chain or branched alkyl, alkenyl or alkynyl having in each case up to 8 carbon atoms, which are optionally substituted by cycloalkyl having 3 to 6 carbon atoms, hydroxyl or by straight-chain or branched alkoxy having up to 6 carbon atoms or phenyl, or
  represent cycloalkyl having 3 to 6 carbon atoms, or
  represent straight-chain or branched acyl or alkoxycarbonyl having in each case up to 8 carbon atoms, benzyloxycarbonyl or carboxyl, or
  represent phenyl, which is optionally substituted up to 3 times in an identical or different manner by halogen, nitro, cyano, hydroxyl, hydroxmethyl, trifluoromethyl or trifluoromethoxy or by straight-chain or branched alkyl or alkoxy having in each case up to 6 carbon atoms, or
  represent the group of the formula $-CO-NR^6R^7$, $B-R^8$ or $-NR^9R^{10}$, wherein
  $R^6$ and $R^7$ are identical or different and denote hydrogen, phenyl, straight-chain or branched alkyl having up to 6 carbon atoms or benzyl, B denotes an oxygen or sulphur atom,
$R^8$ denotes straight-chain or branched alkyl having up to 8 carbon atoms,
$R^9$ and $R^{10}$ are identical or different and have the abovementioned meaning of $R^6$ and $R^7$, or
$R^9$ or $R^{10}$ denotes the $-SO_2R^{11}$ group, wherein
  $R^{11}$ denotes straight-chain or branched alkyl having up to 6 carbon atoms, benzyl or phenyl, which are optionally substituted by methyl,
$R^3$ and $R^4$, including the double bond, form a phenyl or pyridyl ring which is optionally substituted up to 3 times in an identical or different manner by hydroxyl, formyl, carboxyl, halogen, straight-chain or branched acyl or alkoxycarbonyl having in each case up to 8 carbon atoms or straight-chain or branched perfluoroalkyl having up to 6 carbon atoms or by straight-chain or branched alkyl having up to 8 carbon atoms, which in its turn can be substituted by hydroxyl or straight-chain or branched alkoxy having up to 6 carbon atoms, or are substituted by the group of the formula $-CONR^6R^7$, wherein
  $R^6$ and $R^7$ have the abovementioned meaning,
$R^5$ represents hydrogen, nitro, halogen or straight-chain or branched alkyl having up to 8 carbon atoms, or represents straight-chain or branched perfluoroalkyl having up to 6 carbon atoms, or represents a group of the formula $-OR^{12}$, $-NR^{13}R^{14}$ or $-NR^{13}-CO-R^{15}$, wherein
  $R^{12}$ denotes hydrogen, straight-chain or branched alkyl having up to 8 carbon atoms or phenyl,
  $R^{13}$ and $R^{14}$ are identical or different and have the abovementioned meaning of $R^6$ and $R^7$ and
  $R^{15}$ denotes straight-chain or branched alkyl having up to 6 carbon atoms or phenyl,
A represents a 3- to 8-membered saturated heterocyclic ring which is bonded via the nitrogen atom and has up to 2 further hetero atoms from the series comprising S, N and O, and is optionally substituted up to twice in an identical or different manner by a radical of the formula $-NR^{9'}R^{10'}$, $-SO_3H$,

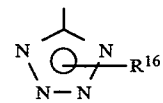

or $-CO-R^{17}$, wherein
$R^{9'}$ and $R^{10'}$ have the abovementioned meaning of $R^9$ and $R^{10}$ and are identical to or different from these,
$R^{16}$ denotes hydrogen, straight-chain or branched alkyl having up to 6 carbon atoms or triphenylmethyl and
$R^{17}$ denotes hydroxyl, straight-chain or branched alkoxy having up to 8 carbon atoms, phenoxy or a group of the formula $-NR^{18}R^{19}$, wherein
  $R^{18}$ and $R^{19}$ are identical or different and denote hydrogen, straight-chain or branched alkyl having up to 6 carbon atoms or phenyl,
and salts thereof.

The sulphonylbenzyl-substituted benzo- and pyridopyridones according to the invention can also be in the form of their salts. Salts with organic or inorganic bases or acids may be mentioned in general here.

Physiologically acceptable salts are preferred in the context of the present invention. Physiologically acceptable salts of the sulphonylbenzyl-substituted benzo- and pyridopyridones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can likewise be metal or ammonium salts of the compounds according to the invention which have a free carboxyl group. Particularly preferred salts are, for example, the sodium, potassium, magnesium or calcium salts, as well as ammonium salts which are derived from ammonia or organic amines, such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, either as enantiomers or as diastereomers. The invention relates both to the enantiomers or diastereomers, and to their particular mixtures. The racemic forms can be resolved, like the diastereomers, into the stereoisomerically uniform constituents in a known manner [compare E. L. Eliel, Stereochemistry of Carbon Compounds, McGraw Hill, 1962].

A 3- to 8-membered saturated heterocyclic ring which is bonded via the nitrogen atom and moreover can contain up to 2 oxygen, sulphur and/or nitrogen atoms as hetero atoms in general represents azetidinyl, piperidyl, morpholinyl, piperazinyl or pyrrolidinyl. 5- and 6-membered rings having one oxygen and/or up to 2 nitrogen atoms are preferred, such as, for example, piperidyl, morpholinyl or pyrrolidinyl. Piperidyl and pyrrolidinyl are particularly preferred.

Preferred compounds of the general formula (I) are those in which $R^1$ and $R^2$ are identical or different and represent hydrogen or cyano, or represent straight-chain or branched alkyl, alkenyl or alkynyl having in each case up to 6 carbon atoms, which are optionally substituted by cyclopropyl, cyclopentyl, cyclohexyl or hydroxyl or by straight-chain or branched alkoxy having up to 4 carbon atoms or phenyl, or represent cyclopropyl, cyclopentyl or cyclohexyl, or represent straight-chain or branched acyl or alkoxycarbonyl having in each case up to 6 carbon atoms, benzyloxycarbonyl or carboxyl, or represent phenyl, which is optionally substituted up to twice in an identical or different manner by fluorine, chlorine, bromine, trifluoromethyl, trifluoromethoxy or hydroxymethyl or by straight-chain or branched alkyl or alkoxy having in each case up to 4 carbon atoms, or represent a group of the formula —CO—$NR^6R^7$, B—$R^8$ or —$NR^9R^{10}$, wherein $R^6$ and $R^7$ are identical or different and denote hydrogen, phenyl, straight-chain or branched alkyl having up to 4 carbon atoms or benzyl, B denotes an oxygen or sulphur atom, $R^8$ denotes straight-chain or branched alkyl having up to 6 carbon atoms, $R^9$ and $R^{10}$ are identical or different and have the abovementioned meaning of $R^6$ and $R^7$, or $R^9$ or $R^{10}$ denotes the —$SO_2R^{11}$ group, wherein $R^{11}$ denotes straight-chain or branched alkyl having up to 4 carbon atoms, phenyl or tolyl, $R^3$ and $R^4$, together and including the double bond, form a phenyl or pyridyl ring which is optionally substituted up to twice in an identical or different manner by hydroxyl, formyl, carboxyl, fluorine, chlorine, bromine, straight-chain or branched acyl or alkoxycarbonyl having in each case up to 6 carbon atoms or straight-chain or branched perfluoroalkyl having up to 4 carbon atoms or by straight-chain or branched alkyl having up to 6 carbon atoms, which in its turn can be substituted by hydroxyl or by straight-chain or branched alkoxy having up to 4 carbon atoms, or are substituted by the group of the formula —CONR$^6$R$^7$, wherein $R^6$ and $R^7$ have the abovementioned meaning, $R^5$ represents hydrogen, nitro, fluorine, chlorine, bromine or straight-chain or branched alkyl having up to 6 carbon atoms, or represents straight-chain or branched perfluoroalkyl having up to 4 carbon atoms, or represents a group of the formula —$OR^{12}$, —$NR^{13}R^{14}$ or —$NR^{13}$—CO—$R^{15}$, wherein $R^{12}$ denotes hydrogen or straight-chain or branched alkyl having up to 6 carbon atoms, $R^{13}$ and $R^{14}$ are identical or different and have the abovementioned meaning of $R^6$ and $R^7$ and $R^{15}$ denotes straight-chain or branched alkyl having up to 6 carbon atoms or phenyl, A represents piperidyl, pyrrolidinyl or morpholinyl which are bonded via the nitrogen atom and are optionally substituted by a radical of the formula —$NR^{9'}R^{10'}$, —$SO_3H$,

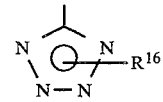

or —CO—$R^{17}$, wherein $R^{9'}$ and $R^{10'}$ have the abovementioned meaning of $R^9$ and $R^{10}$ and are identical to or different from these, $R^{16}$ denotes hydrogen, straight-chain or branched alkyl having up to 4 carbon atoms or triphenylmethyl and $R^{17}$ denotes hydroxyl, straight-chain or branched alkoxy having up to 6 carbon atoms, phenoxy or a group of the formula —$NR^{18}R^{19}$, wherein $R^{18}$ and $R^{19}$ are identical or different and denote hydrogen or straight-chain or branched alkyl having up to 4 carbon atoms, and salts thereof.

Particularly preferred compounds of the general formula (I) are those in which $R^1$ and $R^2$ are identical or different and represent hydrogen or cyano, or represent straight-chain or branched alkyl having up to 4 carbon atoms, which is optionally substituted by cyclopropyl, or represent cyclopropyl or phenyl, or represent straight-chain or branched acyl or alkoxycarbonyl having in each case up to 4 carbon atoms, benzyloxycarbonyl or carboxyl, or represent a group of the formula —CO—$NR^6R^7$, B—$R^8$ or —$NR^9R^{10}$, wherein $R^6$ and $R^7$ are identical or different and denote hydrogen, phenyl, ethyl or benzyl, B denotes an oxygen or sulphur atom, $R^8$ denotes straight-chain or branched alkyl having up to 4 carbon atoms, $R^9$ and $R^{10}$ are identical or different and have the abovementioned meaning of $R^6$ and $R^7$, or $R^9$ or $R^{10}$ denotes the $-SO_2R^{11}$ group, wherein $R^{11}$ denotes methyl, phenyl or tolyl, $R^3$ and $R^4$, together and including the double bond, form a fused-on phenyl or pyridyl ring which is optionally substituted up to twice in an identical or different manner by hydroxyl, carboxyl, fluorine, chlorine, straight-chain or branched acyl or alkoxycarbonyl having in each case up to 4 carbon atoms or straight-chain or branched perfluoroalkyl having up to 3 carbon atoms or by straight-chain or branched alkyl having up to 4 carbon atoms, which in its turn can be substituted by hydroxyl or by straight-chain or branched alkoxy having up to 3 carbon atoms, or are substituted by the group of the formula $-CO-NR^6R^7$, wherein $R^6$ and $R^7$ have the abovementioned meaning, $R^5$ represents hydrogen, nitro, fluorine, chlorine or straight-chain or branched alkyl having up to 4 carbon atoms, or represents straight-chain or branched perfluoroalkyl having up to 3 carbon atoms, or represents a group of the formula $-OR^{12}$, $-NR^{13}R^{14}$ or $-NR^{13}-CO-R^{15}$, wherein $R^{12}$ denotes hydrogen or straight-chain or branched alkyl having up to 4 carbon atoms, $R^{13}$ and $R^{14}$ are identical or different and have the abovementioned meaning of $R^6$ and $R^7$, and $R^{15}$ denotes straight-chain or branched alkyl having up to 6 carbon atoms or phenyl, A represents piperidyl or pyrrolidinyl which are bonded via the nitrogen atom and are optionally substituted by a radical of the formula $-NR^{9'}R^{10'}$, $-SO_3H$,

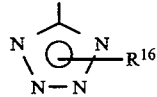

or $-CO-R^{17}$, wherein $R^{9'}$ and $R^{10'}$ have the abovementioned meaning of $R^9$ and $R^{10}$ and are identical to or different from these, $R^{16}$ denotes hydrogen, methyl, ethyl or triphenylmethyl and $R^{17}$ denotes hydroxyl, straight-chain or branched alkoxy having up to 4 carbon atoms, phenoxy or a group of the formula $-NR^{18}R^{19}$, wherein $R^{18}$ and $R^{19}$ are identical or different and denote hydrogen or straight-chain or branched alkyl having up to 3 carbon atoms, and salts thereof.

A process has furthermore been found for the preparation of the compounds of the general formula (I) according to the invention, characterised in that pyridones of the general formula (II)

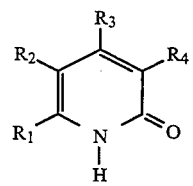

in which $R^1$, $R^2$, $R^3$ and $R^4$ have the abovementioned meaning, are reacted with compounds of the general formula (III)

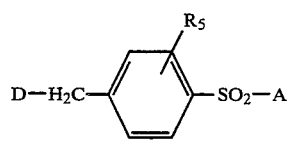

in which $R^5$ and A have the abovementioned meaning and

D represents halogen, preferably bromine, in organic solvents and in the presence of a base and if appropriate a catalyst, and, in the case where $R^{16}$ does not represent hydrogen, an alkylation follows, and, in the case of the acids ($R^{17}=OH$), the corresponding esters are hydrolysed, and, in the case of the esters or amides, an esterification or amidation follows, if appropriate via an activated carboxylic acid stage, and both the substituents $R^1$, $R^2$ and $R^5$ and the substituents of the phenyl and pyridyl ring ($R^3/R^4$) are varied by customary methods.

The process according to the invention can be illustrated by way of example by the following equation:

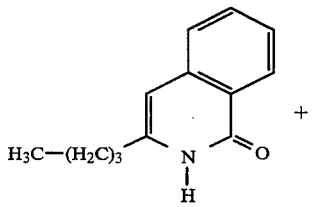

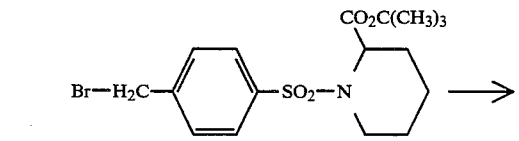

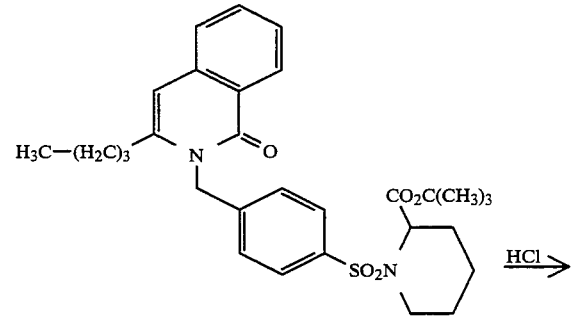

-continued

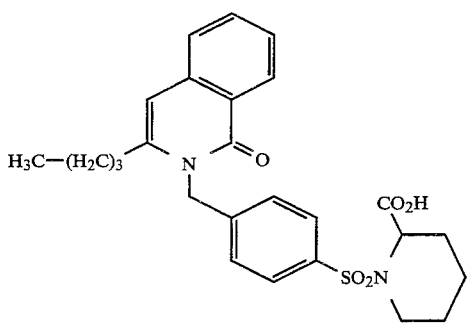

Suitable solvents for the process are customary organic solvents which do not change under the reaction conditions. These include, preferably, ethers, such as diethyl ether, dioxane, tetrahydrofuran, glycol dimethyl ether or 1,2-dimethoxyethane, or hydrocarbons, such as benzene, toluene, xylene, hexane, cyclohexane or petroleum fractions, or halogenohydrocarbons, such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is also possible to use mixtures of the solvents mentioned. Tetrahydrofuran and 1,2-dimethoxyethane are preferred.

Inorganic or organic bases can in general be employed as bases for the process according to the invention. These include, preferably, alkali metal hydroxides, such as, for example, sodium hydroxide, potassium hydroxide or lithium hydroxide, barium hydroxide, alkali metal or alkaline earth metal carbonates, such as sodium carbonate, potassium carbonate, calcium carbonate or caesium carbonate, or alkali metal or alkaline earth metal alcoholates, such as sodium methanolate, potassium methanolate or potassium tert-butylate, or lithium diisopropylamide (LDA), or organic amines (trialkyl($C_1$–$C_6$)amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, or hydrides thereof, such as sodium hydride, as bases. Potassium carbonate, sodium hydride, potassium tertbutylate and caesium carbonate are preferred.

The base is in general employed in an amount of 0.05 mol to 10 mol, preferably 1 mol to 2 mol, per mole of compound of the formula (III).

The process according to the invention is in general carried out in a temperature range from −100° C. to +100° C., preferably from 0° C. to 40° C.

The process according to the invention is in general carried out under normal pressure. However, it is also possible to carry out the process under increased pressure or under reduced pressure (for example in a range from 0.5 to 5 bar).

The triphenylmethyl group is split off with acetic acid or trifluoroacetic acid and water or one of the abovementioned alcohols, or with aqueous hydrochloric acid in the presence of acetone, or likewise with alcohols.

The splitting-off is in general carried out in a temperature range from 0° C. to 150° C., preferably from 20° C. to 100° C., under normal pressure.

Suitable catalysts are potassium iodide or sodium iodide, preferably sodium iodide.

The alkylation is in general carried out with alkylating agents, such as, for example, ($C_1$–$C_6$)-alkyl halides, sulphonic acid esters or substituted or unsubstituted ($C_1$–$C_6$)-dialkyl- or ($C_1$–$C_6$)-diarylsulphonates, preferably methyl iodide or dimethyl sulphate.

The alkylation is in general carried out in one of the abovementioned solvents, preferably in dimethylformamide or dimethoxyethane, in a temperature range from 0° C. to +70° C., preferably from 0° C. to +30° C., under normal pressure.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate, or alkali metal alcoholates, such as sodium methanolate, sodium ethanolate, potassium methanolate, potassium ethanolate or potassium tert-butanolate. Sodium hydroxide, potassium hydroxide or lithium hydroxide are particularly preferably employed.

Suitable solvents for the hydrolysis are water or the organic solvents customary for hydrolysis. These include, preferably, alcohols, such as methanol, ethanol, propanol, isopropanol or butanol, or ethers, such as tetrahydrofuran or dioxane, or dimethylformamide, or dimethyl sulphoxide. Alcohols, such as methanol, ethanol, propanol or isopropanol, are particularly preferably used. It is also possible to employ mixtures of the solvents mentioned. Tetrahydrofuran and methanol are preferred.

If appropriate, the hydrolysis can also be carried out with acids, such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

The hydrolysis is in general carried out under normal pressure. However, it is also possible for it to be carried out under reduced pressure or under increased pressure (for example from 0.5 to 5 bar).

In carrying out the hydrolysis, the base is in general employed in an amount of 1 to 3 mol, preferably 1 to 1.5 mol, per mole of ester. Molar amounts of the reactants are particularly preferably used.

The hydrolysis of tert-butyl esters is in general carried out with acids, such as, for example, hydrochloric acid or trifluoroacetic acid, in the presence of one of the abovementioned solvents and/or water or mixtures thereof, preferably with dioxane or tetrahydrofuran.

In carrying out the reaction, the carboxylates of the compounds according to the invention are formed as intermediate products in the first step and can be isolated. The acids according to the invention are obtained by treatment of the carboxylates with customary inorganic acids. These include, preferably, mineral acids, such as, for example, hydrochloric acid, hydrobromic acid, sulphuric acid or phosphoric acid. In this case, it has proved advantageous in the preparation of the carboxylic acids to acidify the basic reaction mixture of the hydrolysis in a second step without isolation of the carboxylates. The acids can then be isolated in the customary manner. In the case of the basic heterocyclic compounds, the salts of the heterocyclic compounds with the inorganic acids can be obtained by treatment of the solutions of the carboxylates with the abovementioned acids.

The amidation and the sulphonamidation are in general carried out in one of the abovementioned solvents, preferably in tetrahydrofuran or dichloromethane.

If appropriate, the amidation and the sulphonamidation can proceed via the activated stage of acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from $-20°$ C. to $+80°$ C., preferably from $-10°$ C. to $+30°$ C., under normal pressure.

Suitable bases for these reactions are, in addition to the abovementioned bases, preferably triethylamine and/or dimethylaminopyridine, DBU or DABCO.

The base is employed in an amount of 0.5 mol to 10 mol, preferably 1 mol to 2 mol, per mole of corresponding acid or ester.

Acid-binding agents which can be employed for the sulphonamidation are alkali metal or alkaline earth metal carbonates, such as sodium carbonate or potassium carbonate, alkali metal or alkaline earth metal hydroxides, such as, for example, sodium hydroxide or potassium hydroxide, or organic bases, such as pyridine, triethylamine, N-methylpiperidine or bicyclic amidines, such as 1,5-diazabicyclo[3.4.0]non-5-ene (DBN) or 1,5-diazabicyclo[3.4.0]undec-5-ene (DBU). Potassium carbonate is preferred.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphoric anhydride or isobutyl chloroformate or benzotriazolyloxytris-(dimethylamino)phosphoniuan hexylfluorophosphate or phosphonic acid diphenyl ester-amide or methanesulphonyl chloride, if appropriate in the presence of bases, such as triethylamine or N-ethylmorpholine or N-methylpiperidine or dicyclohexylcarbodiimide and N-hydroxysuccinimide [compare J. C. Sheehan, S. L. Ledis, J. Am. Chem. Soc. 95, 875 (1973); F. E. Frerman et al., J. Biol. Chem. 258, 7087–7093 (1983) and N. B. Benoton, K. Kluroda, Int. Pept. Prot. Res., 17, 197 (1981)].

The acid-binding agents and dehydrating reagents are in general employed in an amount of 0.5 to 3 mol, preferably 1 to 1.5 mol, per mole of corresponding carboxylic acids.

The pyridones of the general formula (II) are new and can be prepared, in the case where

[A]

$R^3$ and $R^4$ form a phenyl ring, by a process in which compounds of the general formula (IV)

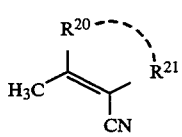

(IV)

in which $R^{20}$ and $R^{21}$ form an optionally substituted phenyl ring, are first converted, by reactions with compounds of the general formula (V)

$$R^{1'}-CO_2-E \qquad (V)$$

in which $R^{1'}$ represents an alkyl, alkenyl or alkinyl radical and E represents $C_1-C_4$-alkyl, preferably methyl, under an inert gas atmosphere, in one of the abovementioned solvents and in the presence of one of the bases likewise mentioned above, and/or catalysts, preferably in ammonia with potassium amide, into the compounds of the general formula (VI)

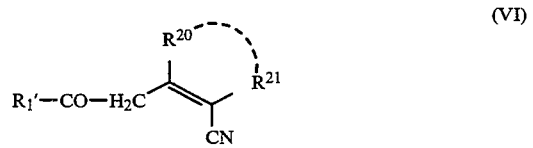

(VI)

in which $R^{1'}$, $R^{20}$ and $R^{21}$ have the abovementioned meaning, which are then cyclised with acids in alcohols, preferably with sulphuric acid in ethanol, and, in the case where $R^1$ does not represent an alkyl, alkenyl or alkinyl radical, the substituent $R^{1'}$ is derivatised by customary methods, and in the case where

[B]

$R^3$ and $R^4$ together form a pyridyl ring, by a process in which, for example, pyridines of the general formula (VII)

(VII)

in which $R^{22}$ and $R^{23}$ form an optionally substituted pyridyl ring, are first converted, by reaction with compounds of the general formula (VIII)

$$CH\equiv C-R^1 \qquad (VIII)$$

in which $R^1$ has the abovementioned meaning, in an autoclave under an inert gas atmosphere in the presence of catalysts/auxiliaries, preferably in the system bis-(triphenylphosphine)-palladium(II) chloride/copper(I) iodide, into the compounds of the general formula (IX)

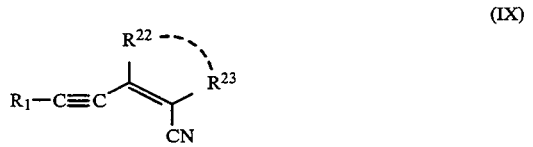

(IX)

in which $R^1$, $R^{22}$ and $R^{23}$ have the abovementioned meaning, which are then either cyclised directly as described under [A], or are first cyclised via the stage of the general formula (X)

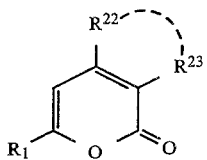
(X)

in which
R¹, R²² and R²³ have the abovementioned meaning,
and are then reacted with ammonia,
and, in the case where R² does not represent hydrogen, the products are derivatised by customary methods,
and if appropriate the phenyl and also the pyridyl substituents mentioned under R³/R⁴ are likewise varied.

The catalysts/auxiliaries are in general employed in an amount of 0.001 mol to 0.5 mol, preferably 0.01 mol to 0.3 mol, in each case per mole of compounds of the general formulae (IV) and (VII).

The bases are in general employed in an amount of 1 mol to 5 mol, preferably 1 mol to 3 mol, in each case per mole of compounds of the general formula (IV).

The reaction temperatures for the individual steps lie in a range from 0° C. to 180° C., preferably from 20 °C. to 150° C.

The reaction can be carried out both under normal pressure and under increased pressure, for example 0.5 to 5 bar, and if appropriate under an inert gas atmosphere, depending on the individual reaction steps.

The compounds of the general formulae (IV), (V) and (VI) are known in most cases or can be prepared by customary methods (compare, for example, J. Org. Chem. 1966, 31, 3807).

The compounds of the general formula (VII) are new in some cases, and can be prepared, for example, by a process in which the corresponding 3-bromo-substituted pyridines are first converted, by reaction with hydrogen peroxide in acetic acid, into the particular pyridine N-oxides, and in a second step, the cyano group is introduced by customary methods, for example using trimethylsilyl cyanide in acetonitrile and in the presence of triethylamine in a temperature range from 20° C. to 120° C., preferably from 60° C. to 100° C. (in this context, compare J. Org. Chem. 1958 23, 1616, and Chem. Pharm. Bull. 1985, 35, 565).

The compounds of the general formula (VIII) are known per se or can be prepared by customary methods.

The compounds of the general formulae (IX) and (X) are known in some cases or are new, and can be prepared, for example, as described above or in accordance with published methods (compare, for example, Chem. Pharm. Bull, 34(7) 2760–5; 33(2), 626–33; Heterocycles 32(5), 1013–16 Indian J. Chem., Sect. B, 20B(5), 376–9; and Chem. Pharm. Bull. 1988, 36, 1890.

The compounds of the general formula (III) are new and can be prepared by a process in which substituted benzylsulphonic acid chlorides of the general formula (XI)

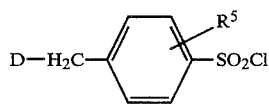
(XI)

in which

R⁵ has the abovementioned meaning and
D represents halogen, preferably bromine,
are reacted with compounds of the general formula (XII)

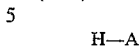
(XII)

in which
A has the abovementioned meaning,
in one of the abovementioned solvents and bases, preferably in dichloromethane with triethylamine.

The reaction is in general carried out in a temperature range from 0° C. to +100° C., preferably from +20° C. to +80° C.

The reaction is in general carried out under normal pressure. However, it is also possible to carry out the reaction under reduced pressure or under increased pressure (for example from 0.5 to 5 bar).

In carrying out the reaction, the base is in general employed in an amount of 1 to 3 mol, preferably 1 to 1.5 mol, per mole of compounds of the general formula (IV). Molar amounts of the reactants are particularly preferably used.

The reaction is in general carried out in a temperature range from −10° C. to +40° C., preferably from −10° C. to 0° C., under normal pressure.

The compounds of the general formulae (XI) and (XII) are known or can be prepared by the customary method.

The compounds of the general formula (I) according to the invention exhibit an unforeseeable, useful pharmacological action spectrum.

The compounds according to the invention have a specific A II-antagonistic action, since they inhibit the binding of angiotensin II to A II receptors. They suppress the vasoconstricting and aldosterone secretion-stimulating effects of angiontensin II. Moreover, they inhibit proliferation of smooth muscle cells.

They can therefore be employed in medicaments for the treatment of arterial hypertension and atherosclerosis. Moreover, they can be employed for the treatment of coronary heart diseases, cardiac insufficiency, disturbances in cerebral performance, ischaemic cerebral diseases, disturbances in peripheral circulation, functional disturbances of the kidney and adrenal, diseases of the respiratory passages of bronchospastic and vascular origin, sodium retention and oedemas.

Investigation of the Inhibition of Agonist-Induced Contraction

Rabbits of both sexes are stunned by a blow to the neck and exsanguinated, or optionally anaesthetised with Nembutal (about 60–80 mg/kg i.v.) and sacrificed by opening the thorax. The thoracic aorta is removed, freed from adhering connective tissue and divided into ring segments 1.5 mm wide, and these are introduced individually, under an initial load of about 3.5 g, into 10 ml organ baths with carbogen-gassed Krebs-Henseleit nutrient solution thermostatically controlled at 37° C. and having the following composition: 119 mmol/l of NaCl; 2.5 mmol/l of $CaCl_2 \times 2$ $H_2O$; 1.2 mmol/l of $KH_2PO_4$; 10 mmol/l of glucose; 4.8 mmol/l of KCl; 1.4 mmol/l of $MgSO_4 \times 7$ $H_2O$ and 25 mmol/l of $NaHCO_3$.

The contractions are recorded isometrically by Statham UC2 cells via a bridge amplifier (from Mülheim or DSM Aalen) and digitised and evaluated by means of an A/D converter (System 570, Keithley Munich). The agonist dose/effect curves (DEC) are plotted hourly.

For each DEC, 3 or 4 individual concentrations are applied to the baths at intervals of 4 minutes. At the end of the DEC and the subsequent wash-out cycles (16 times for in each case about 5 seconds/minute with the abovementioned nutrient solution), a 28-minute rest or incubation phase follows, within which the contractions as a rule reach the starting value again.

The level of the third DEC in the normal case is used as the reference parameter for evaluation of the test substance which is to be investigated in further test runs and which is applied to the baths for the subsequent DECs at the start of the incubation period at a dosage which increases each time. In this procedure, each aortic ring is stimulated for the entire day with always the same agonist.

Agonists and their standard concentrations
Application volume per individual dose = 100 µl):

| | | |
|---|---|---|
| KCl | 22.7; 32.7; 42.7; 52.7 | mmol/l |
| 1-Noradrenaline | $3 \times 10^{-9}; 3 \times 10^{-8}; 3 \times 10^{-7}; 3 \times 10^{-6}$ | g/ml |
| Serotonin | $10^{-8}; 10^{-7}; 10^{-6}; 10^{-5}$ | g/ml |
| B-HT 920 | $10^{-7}; 10^{-6}; 10^{-5}$ | g/ml |
| Methoxamine | $10^{-7}; 10^{-6}; 10^{-5}$ | g/ml |
| Angiotensin II | $3 \times 10^{-9}; 10^{-8}; 3 \times 10^{-8}; 10^{-7}$ | g/ml |

The effect at the particular 3rd=submaximum agonist concentration is taken as a basis for calculation of the $IC_{50}$ (concentration at which the substance to be investigated causes 50% inhibition).

The compounds according to the invention inhibit the contraction of the isolated rabbit aorta induced by angiotensin II as a function of the dose. The contraction induced by potassium depolarisation or other agonists is not inhibited or is inhibited only weakly at high concentrations.

TABLE A

Inhibition of Vasoconstriction on Isolated Aortic Rings From Rabbits In Vitro

Example 2: $IC_{50}$ = 660 nM.

Blood Pressure Measurements on the Angiotensin II-Infused Rat

Male Wistar rats (Moellegaard, Copenhagen, Denmark) having a body weight of 300–350 g are anaesthetised with thiopental (100 mg/kg i.p.). After tracheotomy, a catheter for blood pressure measurement is inserted into the femoral artery and a catheter for angiotensin II infusion and a catheter for administration of the substance are inserted into the femoral veins. After administration of the ganglionic blocker pentolinium (5 mg/kg i.v.), angiotensin II infusion (0.3 µg/kg/minute) is started. As soon as the blood pressure values have reached a stable plateau, the test substances are administered either intravenously, or orally as a suspension or solution in 0.5% tylose. The changes in blood pressure under the influence of the substance are shown as the mean values ± SEM in the table.

Determination of the Antihypertensive Activity on Conscious Hypertensive Rats

The oral antihypertensive activity of the compounds according to the invention was tested on conscious rats with surgically induced unilateral renal arteriostenosis. For this, the right renal artery was constricted with a silver clip of 0.18 mm internal diameter. With this form of hypertension, the plasma renin activity is increased in the first six weeks after the intervention. The arterial blood pressure of these animals was measured bloodlessly using a "tail cuff" at defined intervals of time after administration of the substance. The substances to be tested were administered intragastrally ("orally") by stomach tube in various doses suspended in a tylose suspension. The compounds according to the invention lower the arterial blood pressure of the hypertensive rats in a clinically relevant dosage.

The compounds according to the invention furthermore inhibit specific binding of radioactive angiotensin II as a function of the concentration.

Interaction of the Compounds According to the Invention With the Angiotensin II Receptor on Membrane Fractions of the Adrenal Cortex (Bovine)

Bovine adrenal cortices (AC) which are freshly removed and thoroughly freed from medulla of the capsule are comminuted in sucrose solution (0.32 M) with the aid of an Ultra-Turrax (Janke & Kunkel, Staufen i.B.) to give a coarse membrane homogenate, which is partially purified in two centrifugation steps to give membrane fractions. The investigations in receptor binding are carried out on partially purified membrane fractions of bovine AC with radioactive angiotensin II in an assay volume of 0.25 ml which contains, specifically, the partially purified membranes (50–80 µg), $^3$H-angiotensin II (3–5 nM), test buffer solution (50 mM Tris, pH 7.2) 5 mM $MgCl_2$ and the substances to be investigated. After an incubation time of 60 minutes at room temperature, the non-bound radioactivity of the samples is separated off by means of moistened glass fibre filters (Whatman GF/C) and the bound radioactivity is measured spectrophotometrically in a scintillation cocktail, after the protein has been washed with ice-cold buffer solution (50 mM Tris/HCl, pH 7.4, 5% PEG 6000). The raw data were analysed with computer programs to give $K_i$ and $IC_{50}$ values ($K_i$: $IC_{50}$ values corrected for the radioactivity used; IC50 values: concentration at which the substance to be investigated causes 50% inhibition of the specific binding of the radioligand).

Ex 2: Ki - 1700 nM.

Investigation of the Inhibition of the Proliferation of Smooth Muscle Cells by the Compounds According to the Invention Smooth muscle cells which are obtained from the aortas of rats or pigs by the media explantate technique [R. Ross, J. Cell. Biol. 50, 172, 1971] are used to determine the antiproliferative action of the compounds. The cells are sown in suitable culture dishes, as a rule 24-hole plates, and cultured at 37° C. for 2–3 days in a medium with added serum, 2 mmol L-glutamine and 15 mmol HEPES, pH 7.4, in 5% $CO_2$. Thereafter, the cells are synchronised for 2–3 days by serum withdrawal, and then stimulated into growth with AII, serum or other factors. At the same time, test compounds are added. After 16–20 hours, 1 µCi of $^3$H-thymidine is added, and the incorporation of this substance into the DNA of the cells which can be precipitated with TCA is determined after a further 4 hours.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents.

The therapeutically active compound should be present here in each case in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Administration is effected in the customary manner, preferably orally or parenterally, in particular perlingually or intravenously.

In the case of parenteral use, solutions of the active compound can be employed, using suitable liquid excipient materials.

In general, it has proved advantageous, in the case of intravenous administration, to administer amounts of about 0.001 to 1 mg/kg, preferably about 0.01 to 0.5 mg/kg of body weight, in order to achieve effective results, and in the case of oral administration, the dosage is about 0.01 to 20 mg/kg, preferably 0.1 to 10 mg/kg of body weight. Nevertheless, it may be necessary to deviate from the amounts mentioned if appropriate; that is, depending on the body weight or on the nature of the administration route, on the behaviour of the individual towards the medicament, on the nature of the formulation thereof and on the time or interval at which administration takes place. Thus in some cases it may be sufficient to manage with less than the abovementioned minimum amount, while in other cases the upper limit mentioned has to be exceeded. Where relatively large amounts are administered, it may be advisable to divide these into several individual doses given over the course of the day.

STARTING COMPOUNDS

Example I 2-(2-Oxo-hexyl)-benzonitrile

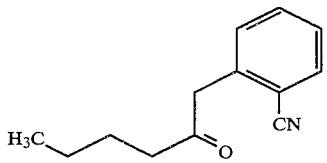

Under argon, potassium (3.8 g, 0.10 mol) is dissolved in ammonia (150 ml), a spatula-tip of iron(III) nitrate is added and the mixture is stirred under reflux for 15 minutes. A solution of 2-tolunitrile (12 ml; 0.10 mol) in ether (25 ml) is added dropwise, and after 10 minutes, a solution of methyl valerate (6.6 ml; 0.050 mol) in ether (25 ml) is added. After one hour, ammonium chloride (6.1 g, 0.12 mol) and ether (25 ml) are added, and the ammonia is evaporated overnight. The suspension is heated briefly, acidified with 6 N hydrochloric acid and extracted with methylene chloride. Drying of the organic phase over sodium sulphate, concentration and silica gel chromatography (hexane:ethyl acetate=5:1) give 3.1 g of a yellow oil (31% of theory).

$R_f$=0.52 (hexane:ethyl acetate=3:1).

Example II

3-Butyl-isoquinolin-1(2H)-one

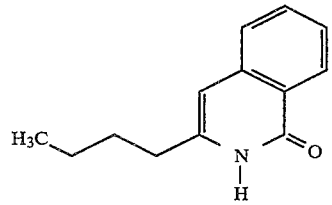

Concentrated sulphuric acid (60 ml) is added to a solution of Example I (3.1 g; 15 mmol) in ethanol/water (19:1; 600 ml), while cooling with ice. After the reaction solution has been heated under reflux for 7 hours, it is poured onto ice and concentrated. Filtration with suction and recrystallisation of the precipitated product from hexane 1.8 g of a white solid (57% of theory).

Melting point: 137° C.

$R_f$=0.28 (hexane:ethyl acetate=3:1).

Example III 2-(2-Oxo-butyl)-benzonitrile

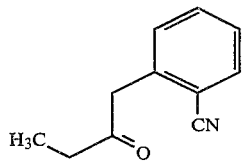

Analogously to Example I, 3.1 g of a yellow oil (36% of theory) are obtained by acylation of 2-tolunitrile (1 ml; 0.10 mol) with methyl propionate (4.8 ml; 50 mmol).

$R_f$=0.46 (hexane:ethyl acetate=3:1)

Example IV

3-Ethyl-isoquinolin-1(2H)-one

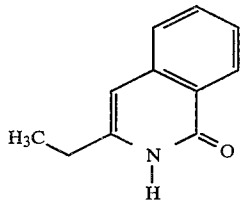

Analogously to Example II, 1.6 g of a solid (52% of theory) are obtained from Example III (3.1 g; 18 mmol).

Melting point: 136° C.

$R_f$=0.13 (hexane:ethyl acetate=3:1).

Example V

2-(Benzoylmethyl)-benzonitrile

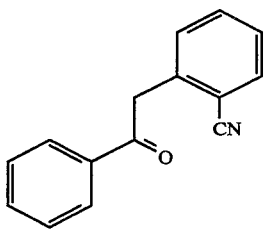

Analogously to Example I, 3.1 g of a white solid (50% of theory) are obtained by acylation of 2-tolunitrile (12 ml; 0.10 mol) with methyl benzoate (6.3 ml; 50 mmol).

Melting point: 109° C.

$R_f$=0.42 (hexane:ethyl acetate=3:1).

Example VI

3-Phenyl-isoquinolin-1(2H)-one

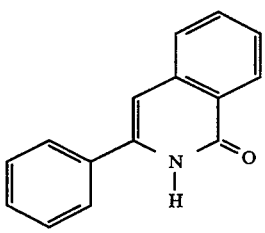

Analogously to Example II, 2.0 g of a solid (46% of theory) are obtained from Example V (4.3 g; 19 mmol).

Melting point: 105° C.

$R_f$=0.15 (hexane:ethyl acetate=3:1).

Example VII

3-Bromopyridine N-oxide

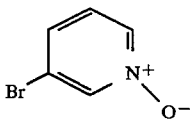

Hydrogen peroxide:H₂O (30:70; 50 ml) is added to a solution of 3-bromopyridine (3 ml; 0.32 mol) in glacial acetic acid (250 ml), and the mixture is stirred at 100° C. After 3 hours and 19 hours, further hydrogen peroxide:H₂O (30:70; 25 ml each time) is added and the mixture is heated at 100° C. for a further 4 hours. The reaction solution is concentrated to one third of the volume, topped up again with water and concentrated to dryness. The residue is dissolved in methylene chloride and the solution is washed with sodium carbonate solution. Saturation of the aqueous phase with sodium chloride, extraction with methylene chloride and drying and concentration of the combined organic phases give 43 g of an oil (77% of theory).

$R_f$=0.37 (methylene chloride:methanol=20:1).

Example VIII

3-Bromo-2-cyanopyridine

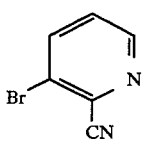

A solution of Example VII (22 g; 0.12 mol), trimethylsilyl cyanide (45 ml; 0.36 mmol) and triethylamine (33 ml; 0.24 mol) in acetonitrile (120 ml) is heated under reflux for 4 hours and concentrated, and the residue is poured onto 3 N sodium carbonate solution. Extraction with methylene chloride and drying and concentration of the organic phases give, after recrystallisation from hexane/ethyl acetate, 17 g of a solid (79% of theory).

Melting point: 92° C.

$R_f$=0.31 (hexane:ethyl acetate=3:1).

Example IX

2-Cyano-3-hex-1-inylpyridine

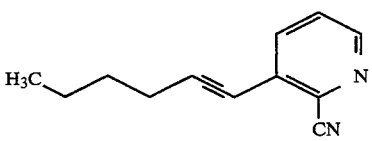

The compound from Example VIII (4.8 g; 26 mmol), 1-hexine (3.6 ml; 31 mmol), bis-(triphenylphosphine)-palladium(II) chloride (0.42 g; 0.60 mmol) and copper(I) iodide (0.21 g; 1.1 mmol) are flushed with nitrogen and heated at 120° C. for 5 hours in an autoclave. Partitioning of the reaction mixture between water and ether and drying and concentration of the organic phase give, after silica gel chromatography (hexane:ethyl acetate=4:1), 0.76 g of an oil (16% of theory).

$R_f$=0.60 (hexane:ethyl acetate=3:1).

Example X

4-(Bromomethyl)benzene-sulphonyl chloride

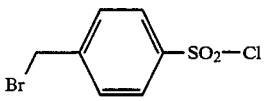

38.1 g (0.2 mol) of 4-methylbenzenesulphonyl chloride are dissolved in 300 ml of carbon tetrachloride, 35.6 g (0.2 mol) of N-bromosuccinimide are added and, after addition of 0.2 g (1.2 mmol) of azobisisobutyronitrile (AIBN),the mixture is heated under reflux for 4 hours. After cooling, the solids are filtered off and the filtrate is freed from the solvent. Flash chromatography (petroleum ether/toluene 4:1, 50 μm particle size) and subsequent recrystallisation from 100 ml of cyclohexane give 24.0 g (45% of theory) of the title compound. $R_f$=0.75 (toluene).

Example XI 4-(Bromomethyl)-3-chlorobenzenesulphonyl chloride

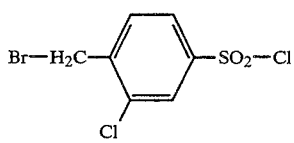

45.9 g (0.2 mol) of sodium 3-chloro-4-methylbenzenesulphonate are mixed with 83.3 g (0.4 mol) of phosphorus pentachloride and the mixture is heated at an oil bath temperature of 140° C. for 30 minutes. 500 ml of toluene are added, while hot, and the solution formed is heated to the boiling point and, after cooling, poured onto ice. The organic phase is separated off and washed with water (2×200 ml). After drying over MgSO₄, it is filtered and all the volatile contents are stripped off in vacuo. The resulting residue is purified by flash chromatography (petroleum ether/toluene 4:1, 50 µ particle size). 24.9 g of a product which is immediately reacted further are obtained:

The product is taken up in 200 ml of carbon tetrachloride and, after addition of 19.6 g (0.11 mol) of N-bromosuccinimide and 0.1 g (0.6 mmol) of AIBN, the mixture is heated under reflux for 6 hours. After cooling, the solids are filtered off and the filtrate is freed from the solvent. Flash chromatography (petroleum ether/toluene 4:1, 50 µ particle size) gives 21.2 g (35%) of the title compound.

$R_f$=0.32 (petroleum ether/dichloromethane 4:1).

Example XII 4-(Bromomethyl)-benzenesulphonyl-N-pyrrolidinide

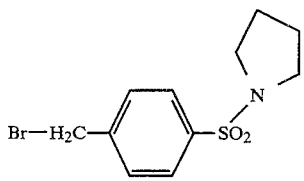

5.3 g (0.02 mol) of the compound from Example X are dissolved in 200 ml of dichloromethane and 4.0 g (0.04 mol) of triethylamine, and, after addition of 1.4 g (0.02 mol) of pyrrolidine in 50 ml of dichloromethane at 0° C., the mixture is subsequently stirred at 0° C. for 1 hour. It is extracted with 2 N HCl (2×100 ml) and H₂O (2×100 ml), dried over MgSO₄ and filtered, and all the volatile contents are evaporated off in vacuo.

Yield: 5.4 g (89% of theory).
$R_f$=0.09 (toluene).

Example XIII 4-(Bromomethyl)benzenesulphonyl-N-piperidinide

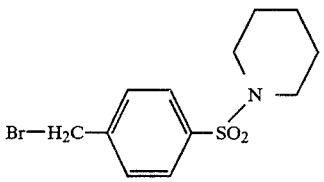

Analogously to the instructions of Example XII, 1.0 g (81% of theory) of the title compound are obtained from 1.1 g (4 mmol) of the compound from Example 1 and 0.34 g (4 mmol) of piperidine.

$R_f$=0.14 (toluene).

Example XIV (S)-4-(Bromomethyl)-benzenesulphonyl-N-2-(tert-butoxycarbonyl)pyrrolidinide

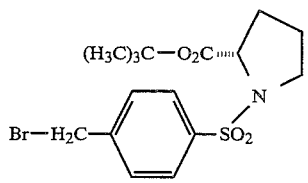

Analogously to the instructions of Example XII, 9.1 g (84% of theory) of the title compound are obtained from 7.25 g (27 mmol) of the compound from Example I and 4.6 g (27 mmol) of S-proline tert-butyl ester.

$R_f$=0.66 (petroleum ether/ethyl acetate 7:3).

Example XV rac-4-(Bromomethyl)-benzenesulphonyl-N-2-(tert-butoxycarbonyl)piperidinide

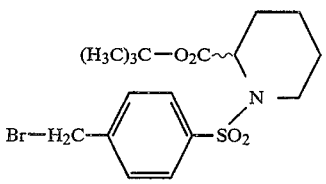

Analogously to the instructions of Example XII, 7.4 g (59% of theory) of the title compound are obtained from 8.0 g (30 mmol) of the compound from Example I and 5.5 g (30 mmol) of rac-pipecolinic acid tert-butyl ester.

$R_f$=0.53 (petroleum ether/ethyl acetate 5:1).

Example XIV (S)-4-(Bromomethyl)-3-chlorobenzenesulphonyl-N-2-(tertbutoxycarbonyl)pyrrolidinide

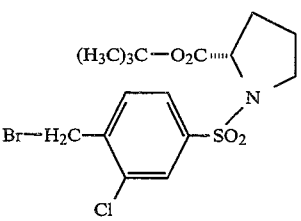

Analogously to the instructions of Example XII, 13.9 g (96% of theory) of the title compound are obtained from 10.0 g (33 mmol) of the compound from Example II and 5.7 g (33 mmol) of S-proline tert-butyl ester.

$R_f$=0.55 (petroleum ether/ethyl acetate 7:3).

Example XVII rac-4-(Bromomethyl)-3-chlorobenzenesulphonyl-N-2-(tertbutoxycarbonyl)piperidinide

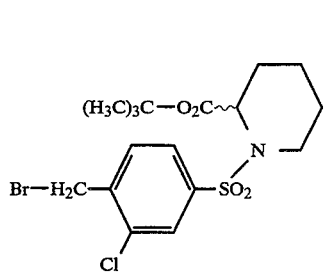

Analogously to the instructions of Example XII, 14.6 g (98% of theory) of the title compound are obtained from 10.0 g (33 mmol) of the compound from Example II and 6.1 g (33 mmol) of rac-pipecolinic acid tert-butyl ester.

$R_f$=0.6 (petroleum ether/ethyl acetate 7:3).

PREPARATION EXAMPLES

Example 1

N-4-[3-Butyl-1,2-dihydro-1-oxo-isoquinolin-2-yl-methyl]3-chlorophenylsulphonylproline tert-butyl ester

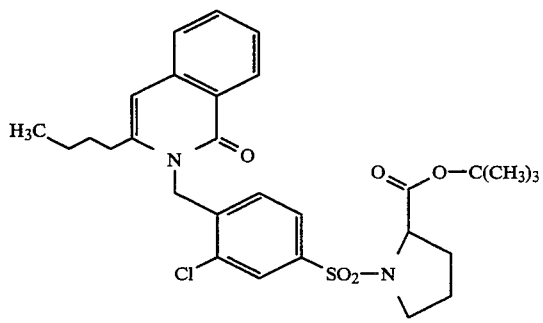

The compound from Example II (710 mg; 1.35 mmol) is dissolved in dimethoxyethane (25 ml), the product from Example XVI (1.86 g; 4.24 mmol) and caesium carbonate (1.38 g; 4.24 mmol) are added, and the mixture is stirred overnight. After two additions of the same amount of caesium carbonate and stirring for a further two days, the reaction solution is concentrated and the residue is partitioned between water and ethyl acetate. The organic phase is dried with sodium sulphate and concentrated, and the residue is chromatographed over silica gel (hexane:ethyl acetate=4:1), in order to give 0.80 g of a solid (40% of theory).

$R_f$=0.28 (hexane:ethyl acetate=3:1).

Example 2

N-4-[3-Butyl-1,2-dihydro-1-oxo-isoquinolin-2-yl-methyl]3-chlorophenylsulphonylproline

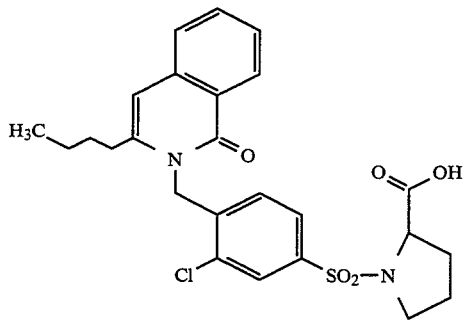

The product from Example 1 (756 mg; 1.35 mmol) is dissolved in methylene chloride (40 ml), and trifluoroacetic acid (40 ml) is added. After 2 hours, the reaction solution is concentrated, the residue is dissolved in ethyl acetate, and the solution is washed with 1 N potassium hydrogen sulphate solution and dried with sodium sulphate. Concentration gives 0.68 g of a solid (100% of theory).

$R_f$=0.34 (methylene chloride:methanol=10:1).

We claim:

1. Sulphonylbenzyl-substituted benzo- or pyridopyridone of the formula

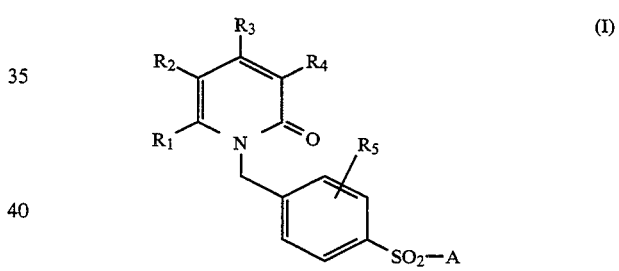

(I)

in which $R^1$ and $R^2$ are identical or different and represent hydrogen or cyano, or represent straight-chain or branched alkyl, alkenyl or alkynyl having in each case up to 8 carbon atoms, which are optionally substituted by cycloalkyl having 3 to 6 carbon atoms, hydroxyl or by straight-chain or branched alkoxy having up to 6 carbon atoms or phenyl, or represent cycloalkyl having 3 to 6 carbon atoms, or represent straight-chain or branched acyl or alkoxycarbonyl having in each case up to 8 carbon atoms, benzyloxycarbonyl or carboxyl, or represent phenyl, which is optionally substituted up to 3 times in an identical or different manner by halogen, nitro, cyano, hydroxyl, hydroxymethyl, trifluoromethyl or trifluoromethoxy or by straight-chain or branched alkyl or alkoxy having in each case up to 6 carbon atoms, or represent the group of the formula —CO—NR$^6$R$^7$, B—R$^8$ or —NR$^9$R$^{10}$, wherein R$^6$ and R$^7$ are identical or different and denote hydrogen, phenyl, straight-chain or branched alkyl having up to 6 carbon atoms or benzyl, B denotes an oxygen or sulphur atom, R⁸ denotes straight-chain or branched alkyl having up to 8 carbon atoms,
  R⁹ and R¹⁰ are identical or different and have the abovementioned meaning of R⁶ and R⁷ or
  R⁹ or R¹⁰ denotes the —SO₂R¹¹ group, wherein
    R¹¹ denotes straight-chain or branched alkyl having up to 6 carbon atoms, benzyl or phenyl, which are optionally substituted by methyl,
R³ and R⁴, including the double bond, form a phenyl or pyridyl ring which is optionally substituted up to 3 times in an identical or different manner by hydroxyl, formyl, carboxyl, halogen, straight-chain or branched acyl or alkoxycarbonyl having in each case up to 8 carbon atoms or straight-chain or branched perfluoroalkyl having up to 6 carbon atoms or by straight-chain or branched alkyl having up to 8 carbon atoms, which in its turn can be substituted by hydroxyl or straight-chain or branched alkoxy having up to 6 carbon atoms, or are substituted by the group of the formula —CONR⁶R⁷, wherein
  R⁶ and R⁷ have the abovementioned meaning,
R⁵ represents hydrogen, nitro, halogen or straight-chain or branched alkyl having up to 8 carbon atoms, or
  represents straight-chain or branched perfluoroalkyl having up to 6 carbon atoms, or
  represents a group of the formula —OR¹², —NR¹³R¹⁴ or —NR¹³—CO—R¹⁵, wherein
    R¹² denotes hydrogen, straight-chain or branched alkyl having up to 8 carbon atoms or phenyl,
    R¹³ and R¹⁴ are identical or different and have the abovementioned meaning of R⁶ and R⁷ and
    R¹⁵ denotes straight-chain or branched alkyl having up to 6 carbon atoms or phenyl,
A represents a 3- to 8-membered saturated heterocyclic ring which is bonded via the nitrogen atom and has up to 2 further hetero atoms from the series comprising S, N and O, and is optionally substituted up to twice in an identical or different manner by a radical of the formula —NR⁹'R¹⁰', —SO₃H,

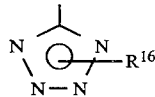

or —CO—R¹⁷, wherein
  R⁹' and R¹⁰' have the abovementioned meaning of R⁹ and R¹⁰ and are identical to or different from these,
  R¹⁶ denotes hydrogen, straight-chain or branched alkyl having up to 6 carbon atoms or triphenylmethyl and
  R¹⁷ denotes hydroxyl, straight-chain or branched alkoxy having up to 8 carbon atoms, phenoxy or a group of the formula —NR¹⁸R¹⁹, wherein
    R¹⁸ and R¹⁹ are identical or different and denote hydrogen, straight-chain or branched alkyl having up to 6 carbon atoms or phenyl,
or a salt thereof.

2. Sulphonylbenzyl-substituted benzo- or pyridopyridone according to claim 1, wherein
  R¹ and R² are identical or different and represent hydrogen or cyano, or
    represent straight-chain or branched alkyl, alkenyl or alkynyl having in each case up to 6 carbon atoms, which are optionally substituted by cyclopropyl, cyclopentyl, cyclohexyl or hydroxyl or by straight-chain or branched alkoxy having up to 4 carbon atoms or phenyl, or
    represent cyclopropyl, cyclopentyl or cyclohexyl, or represent straight-chain or branched acyl or alkoxycarbonyl having in each case up to 6 carbon atoms, benzyloxycarbonyl or carboxyl, or
    represent phenyl, which is optionally substituted up to twice in an identical or different manner by fluorine, chlorine, bromine, trifluoromethyl, trifluoromethoxy or hydroxymethyl or by straight-chain or branched alkyl or alkoxy having in each case up to 4 carbon atoms, or
    represent a group of the formula —CO—NR⁶R⁷, B—R⁸ or —NR⁹R¹⁰, wherein
      R⁶ and R⁷ are identical or different and denote hydrogen, phenyl, straight-chain or branched alkyl having up to 4 carbon atoms or benzyl,
      B denotes an oxygen or sulphur atom,
      R⁸ denotes straight-chain or branched alkyl having up to 6 carbon atoms,
      R⁹ and R¹⁰ are identical or different and have the abovementioned meaning of R⁶ and R⁷, or R⁹ or R¹⁰ denotes the —SO₂R¹¹ group, wherein
        R¹¹ denotes straight-chain or branched alkyl having up to 4 carbon atoms, phenyl or tolyl,
  R³ and R⁴, together and including the double bond, form a phenyl or pyridyl ring which is optionally substituted up to twice in an identical or different manner by hydroxyl, formyl, carboxyl, fluorine, chlorine, bromine, straight-chain or branched acyl or alkoxycarbonyl having in each case up to 6 carbon atoms or straight-chain or branched perfluoroalkyl having up to 4 carbon atoms or by straight-chain or branched alkyl having up to 6 carbon atoms, which in its turn can be substituted by hydroxyl or by straight-chain or branched alkoxy having up to 4 carbon atoms, or are substituted by the group of the formula —CONR⁶R⁷, wherein
    R⁶ and R⁷ have the abovementioned meaning,
  R⁵ represents hydrogen, nitro, fluorine, chlorine, bromine or straight-chain or branched alkyl having up to 6 carbon atoms, or
    represents straight-chain or branched perfluoroalkyl having up to 4 carbon atoms, or
    represents a group of the formula —OR¹², —NR¹³R¹⁴ or —NR¹³—CO—R¹⁵, wherein
      R¹² denotes hydrogen or straight-chain or branched alkyl having up to 6 carbon atoms,
      R¹³ and R¹⁴ are identical or different and have the abovementioned meaning of R⁶ and R⁷ and
      R¹⁵ denotes straight-chain or branched alkyl having up to 6 carbon atoms, or phenyl,
  A represents piperidyl, pyrrolidinyl or morpholinyl which are bonded via the nitrogen atom and are optionally substituted by a radical of the formula —NR⁹'R¹⁰', —SO₃H,

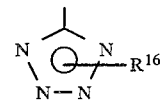

or —CO—R¹⁷, wherein

R⁹' and R¹⁰' have the abovementioned meaning of R⁹ and R¹⁰ and are identical to or different from these, R¹⁶ denotes hydrogen, straight-chain or branched alkyl having up to 4 carbon atoms or triphenylmethyl and R¹⁷ denotes hydroxyl, straight-chain or branched alkoxy having up to 6 carbon atoms, phenoxy or a group of the formula —NR¹⁸R¹⁹, wherein R¹⁸ and R¹⁹ are identical or different and denote hydrogen or straight-chain or branched alkyl having up to 4 carbon atoms, or a salt thereof.

3. Sulphonylbenzyl-substituted benzo- or pyridopyridone according to claim 1, wherein R¹ and R² are identical or different and represent hydrogen or cyano, or represent straight-chain or branched alkyl having up to 4 carbon atoms, which is optionally substituted by cyclopropyl, or represent cyclopropyl or phenyl, or represent straight-chain or branched acyl or alkoxycarbonyl having in each case up to 4 carbon atoms, benzyloxycarbonyl or carboxyl, or represent a group of the formula —CO—NR⁶R⁷, B—R⁸ or —NR⁹R¹⁰, wherein R⁶ and R⁷ are identical or different and denote hydrogen, phenyl, ethyl or benzyl, B denotes an oxygen or sulphur atom, R⁸ denotes straight-chain or branched alkyl having up to 4 carbon atoms, R⁹ and R¹⁰ are identical or different and have the abovementioned meaning of R⁶ and R⁷, or R⁹ or R¹⁰ denotes the —SO₂R¹¹ group, wherein R¹¹ denotes methyl, phenyl or tolyl, R³ and R⁴, together and including the double bond, form a fused-on phenyl or pyridyl ring which is optionally substituted up to twice in an identical or different manner by hydroxyl, carboxyl, fluorine, chlorine, straight-chain or branched acyl or alkoxycarbonyl having in each case up to 4 carbon atoms or straight-chain or branched perfluoroalkyl having up to 3 carbon atoms or by straight-chain or branched alkyl having up to 4 carbon atoms, which in its turn can be substituted by hydroxyl or by straight-chain or branched alkoxy having up to 3 carbon atoms, or are substituted by the group of the formula —CO—NR⁶R⁷, wherein R⁶ and R⁷ have the abovementioned meaning, R⁵ represents hydrogen, fluorine, chlorine or straight-chain or branched alkyl having up to 4 carbon atoms, or represents straight-chain or branched perfluoroalkyl having up to 3 carbon atoms, or represents a group of the formula —OR¹², —NR¹³R¹⁴ or —NR¹³—CO—R¹⁵, wherein R¹² denotes hydrogen or straight-chain or branched alkyl having up to 4 carbon atoms, R¹³ and R¹⁴ are identical or different and have the abovementioned meaning of R⁶ and R⁷, and R¹⁵ denotes straight-chain or branched alkyl having up to 6 carbon atoms or phenyl, A represents piperidyl or pyrrolidinyl which are bonded via the nitrogen atom and are optionally substituted by a radical of the formula —NR⁹'R¹⁰', —SO₃H,

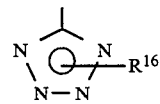

or —CO—R¹⁷, wherein

R⁹' and R¹⁰' have the abovementioned meaning of R⁹ and R¹⁰ and are identical to or different from these, R¹⁶ denotes hydrogen, methyl, ethyl or triphenylmethyl and R¹⁷ denotes hydroxyl, straight-chain or branched alkoxy having up to 4 carbon atoms, phenoxy or a group of the formula —NR¹⁸R¹⁹, wherein R¹⁸ and R¹⁹ are identical or different and denote hydrogen or straight-chain or branched alkyl having up to 3 carbon atoms, or a salt thereof.

4. A compound according to claim 1 wherein such compound is N-4-[3-butyl-1,2-dihydro-1-oxo-isoquinolin-2-yl-methyl]-3-chlorophenylsulphonylproline of the formula

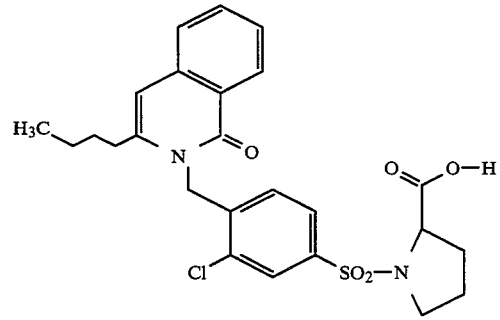

and salts thereof.

5. A compound according to claim 1, wherein such compound is N-4-[3-butyl-1,2-dihydro-1-oxo-isoquinolin-2-yl-methyl]-3-chlorophenylsulphonyl proline tert-butyl ester of the formula:

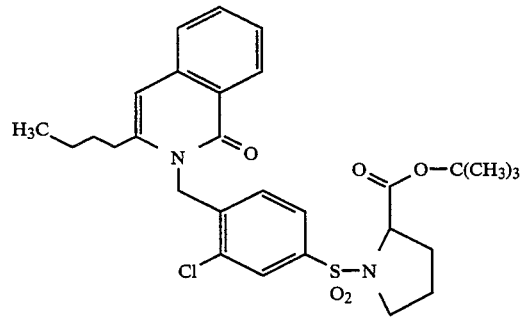

or a salt thereof.

6. A composition for the treatment of arterial hypertension and atherosclerosis comprising an amount effective therefore of a compound or salt thereof according to claim 1 and a pharmacologically acceptable diluent.

7. The method of treating arterial hypertension and atherosclerosis in a patient in need thereof which comprises administering to such patient an amount effective therefore of a compound or salt thereof according to claim 1.

* * * * *